United States Patent [19]

Klug

[11] 4,367,950
[45] Jan. 11, 1983

[54] COMBINED AEROSOL MONITOR AND CALIBRATEABLE LIGHT RAY SCATTERING REFERENCE ROD

[75] Inventor: Jerry J. Klug, Rosemount, Minn.

[73] Assignee: The United States of America as represented by the Secretary of the Interior, Washington, D.C.

[21] Appl. No.: 219,704

[22] Filed: Dec. 24, 1980

[51] Int. Cl.³ .............................................. G01N 21/53
[52] U.S. Cl. .................................... 356/338; 356/243
[58] Field of Search ................ 356/338, 339, 341, 243

[56] References Cited

U.S. PATENT DOCUMENTS 3,992,102 11/1976 Kajii ...................................... 356/338
4,232,967 11/1980 Grackev et al. ................. 356/243 X

FOREIGN PATENT DOCUMENTS 2022282 12/1979 United Kingdom ................. 356/243

Primary Examiner—John K. Corbin
Assistant Examiner—Matthew W. Koren
Attorney, Agent, or Firm—Thomas Zack; Donald A. Gardiner

[57] ABSTRACT

A calibrateable light ray scattering reference rod utilized in a light scattering dust monitor. This light ray rod scatters an amount of light equivalent to a given concentration of dust. Adjustability is provided so that several concentrations of dust can be represented. This adjustment is accomplished by moving a threaded opaque slug axially inside the translucent rod.

2 Claims, 3 Drawing Figures

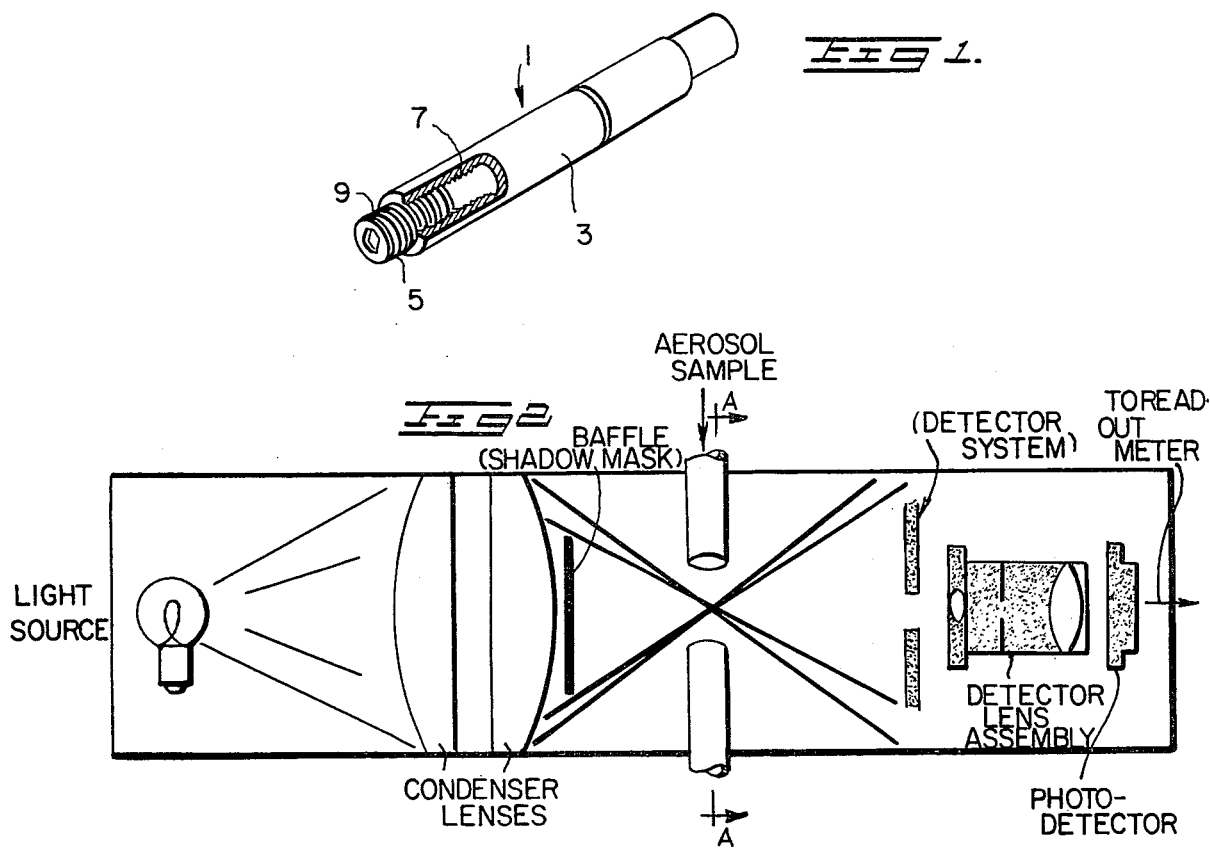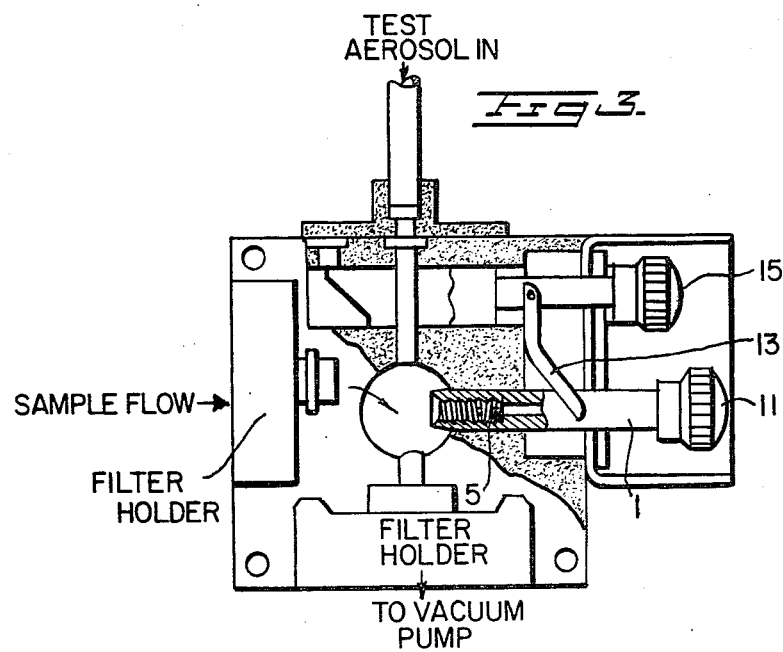

COMBINED AEROSOL MONITOR AND CALIBRATEABLE LIGHT RAY SCATTERING REFERENCE ROD

BACKGROUND OF THE INVENTION

1. Field of the Invention

This invention is an adjustable light scattering rod.

2. Description of the Prior Art

Calibration instruments used for calibrating light scattering analyzers are known in the art. For example, in U.S. Pat. No. 3,742,899 to David K. Longhenry there is provided a device which determines whether a light scattering photometering analyzer is accurately performing. This is accomplished by passing a nested group of wedge-shape sheets through the analyzer. These sample sheets of highly transparent and gray neutral filter glasses have been previously measured by a standard invention instrument to be sure they fall into the operating range of the instrument under investigation. In this way standard readings can be used to determine if the instrument is properly operating within the range of the samples.

Another device is the atmospheric pollution monitor disclosed in U.S. Pat. No. 3,860,818 to A. F. Stalder et al. In the instrument disclosed therein, filters mounted in a rotating chopper are used to provide a range of opacity which can be used to compare samples.

In this invention, the adjustable invention scatterer rod provides a way to periodically check the calibration of a light scattering dust monitor (monitor). Initially the monitor is calibrated by adjusting its electrical gain until its readout meter agrees with the known concentration of the aerosol being sampled. Next, the scatterer rod is inserted into the light cone of the monitor to cause scattering of light. The scatterer rod is then adjusted by its calibrating screw until the monitor meter readout is the same as that of the known concentration. This adjusted scatterer rod then becomes the reference which can be used as a field calibrator checker. The prior art completely fails to suggest or disclose such an adjustable scatter calibration rod for use with a light scattering device.

SUMMARY OF THE INVENTION

The adjustable light ray scattering rod forming the subject matter of this invention is used to calibrate a conventional light ray scattering device. Essentially, once the rod is placed so that it can scatter the light in the light scattering device, a movable slug internally threadedly mounted in the rod is moved until readings taken by the light scattering device agree with previously taken reference readings from a known aerosol sample. This calibrates the rod and its light scattering device for that sample. In the preferred embodiment, the rod was made of a translucent material and the slug of an opaque material.

The primary object of this invention is an improved calibrateable light ray scattering reference rod.

DESCRIPTION OF THE DRAWINGS

FIG. 1 illustrates the preferred embodiment for the light scattering rod, per se.

FIG. 2 is a schematic illustration of the typical environment in which the FIG. 1 embodiment can be used.

FIG. 3 depicts, in partial cross sectional view, how the embodiment of FIG. 1 would be mounted in FIG. 2 as viewed from lines A—A.

The light scattering rod 1 (FIG. 1) is made up of two basic components. These are the main elongated scatterer rod 3 and the calibration slug 5. The slug is mounted in the hollow exterior of the rod by two sets of engaging threads. One set of threads 7 are internally of the hollow rod and extend partially along the length of the rod. In the preferred embodiment, this rod was made from a translucent plastic material and the slug from an opaque material. The external surface of the slug has the other set of threads 9 which are complementary and engage the rod's threads.

When properly placed in a light scattering device monitor, such as that schematically shown in FIG. 2, the preferred embodiment described with respect to FIG. 1 scatters an amount of light equivalent to a given concentration in the aerosol sample. Adjustment of the scatterer rod is accomplished by turning the axially mounted slug relative to the fixed threads of the rod. Usually this adjustment is made so that several concentrations or different types (particle size and shape, reflective index, etc.) of dust or moisture content can be represented. This adjustment is made and then, by looking at the readings on a readout meter from a known reference sample of aerosol having known concentrations, made the same as those readings. Once established, the reading on the calibrated monitor/rod can be used as a reference for the known concentration in spite of small differences in the electronics and optics from one dust monitor to another.

FIG. 2 schematically illustrates a typical light scatterer device monitor such as would be used with my invention. It is representative of many commercial models presently on the market such as Model No. TDA-9A made by Air Techniques, Inc., of Baltimore, Md. What this monitor does—the present invention is not shown in FIG. 2—is to receive light from the light source and then with the condenser lens assembly and shadow mask create a focused cone of light in the region of the aerosol sample flow path. As the aerosol samples moves from the bottom of the figure to the top, it passes through the cone of light and scatters some light into the shadow cast by the shadow mask. This scattered light is observed by the detector lens assembly (shown to the right) and then transmitted to the photodetector. Depending on the amount of scatter and characteristics of the photodetector, an electric signal is generated proportional to the quantity of aerosol and displayed on a readout meter (not shown). Once the monitor has been calibrated with the reference aerosol sample and reference scatterer rod, the same adjustable scatterer rod provides a way to accurately and periodically check the calibration of the monitor.

FIG. 3 is a view of a monitor using the reference scatterer rod, as would be viewed along line A—A of FIG. 2. It illustrates how the scatterer rod would be positioned in the FIG. 2 schematic if it were used therein. Note that the reference scatterer rod is not shown in FIG. 2. The reference scatterer rod of FIG. 3 is shown in its nonoperational (or retracted) mode and would be positioned perpendicular to the plane of the paper if it were shown in the schematic of FIG. 2.

Initially the monitor of FIG. 3 is calibrated by gravimetric or other means with the reference scatterer rod in the retracted position shown with its housing frontal section cut away for ease in understanding. The test aerosol is drawn into the monitor, through the airflow valve 15, through the light cone focal point and onto the filter contained in the monitor, or other suitable filter, where it is collected for subsequent analysis. In this particular illustrated monitor design, an interlock mechanism 13 prevents the scatterer rod from being inserted into the light cone focal point when the airflow valve 15 is in the aerosol sampling position as shown. With the aerosol sample flowing through the monitor, the electrical gain is adjusted until the monitor readout meter agrees with the known aerosol concentration. Then the airflow valve 15 is retracted and the reference scatterer 1 is inserted into the light cone focal point. With the airflow valve 15 in this position, the sample flow enters through the filter in the filter holder on the left side of FIG. 3, passes through the light cone focal point and exits through the filter in the holder at the bottom of FIG. 3. With clean air only flowing through the monitor as described, the knob 11 is removed and the slug 5 is adjusted until the readout meter agrees with the previously established calibration concentration. Once the reference rod scatterer is calibrated for a known sample of aerosol, it can be used as a field check for the monitor. Should the monitor's lenses become coated with dust, the meter readout will probably decrease because less light is available. This can be compensated for by increasing the electrical gain of the monitor with the reference scatterer rod serving as the bench mark for this adjustment. Since the reference scatterer rod is adjustable, each separate monitor can be set to the same calibration reference value regardless of the individual differences in monitors caused by the light intensity pickup differences, the differences in the focussing of their respective lenses, the different photodetectors' sensitivity or the differences in composition of their respective scatterer rods. Without the adjustability of each rod, a calibration reference value for each monitor would have to be recorded for future calibration checks. The adjustability feature also allows the monitor to be calibrated at any concentration of particular interest within the range of the instrument, and allows the reference scatterer or bench mark to be adjusted to this same concentration of interest.

The primary purpose for which this invention was designed and developed was to check the performance of dust monitors used in coal mines. However, it could just as well be used with any type of monitor which employs light scattering techniques and aerosols. The term aerosol is used herein to indicate any type of suspension of particles or liquids in a gas. This would, of course, include coal dust in the ambient air of a mine.

It should be very apparent that many changes can be made to the materials, designs, and other variables for the preferred embodiment shown in FIG. 1. Also, the details of the dust monitor described as being useable with the preferred embodiment should in no way be restricted to the exemplary embodiment of FIG. 2. None of these changes or described devices should be used to limit the scope and extent of the invention which is to be measured only by the claims that follows.

I claim:

1. An adjustable removable light scattering rod in combination with a light scattering aerosol monitor comprising:

a monitor for measuring the concentration of an aerosol;

an elongated light transmitting hollow rod member having an internal threaded portion at least along part of the hollow interior wall thereof, said rod being removably mounted in the monitor and capable of being movable when mounted to intersect the aerosol concentration being monitored; and a movable calibration light intensity reducing slug with external threads thereon and complementary shaped to engage the threads of the rod member, said slug being mounted in the rod and axially adjustable with respect to the rod by moving its threads with respect to those of the rod whereby the slug and rod can be calibrated against a known sample aerosol concentration for the monitor which calibration can be used as a field check at a later time for the monitor.

2. The rod of claim 1 wherein the rod is made of a translucent material and the slug of a opaque material.

* * * * *